United States Patent [19]

Cobb et al.

[11] 4,179,471

[45] Dec. 18, 1979

[54] CATALYTIC ALKYLATION OF ALKYL-SUBSTITUTED AROMATICS WITH MONOOLEFINS

[75] Inventors: Raymond L. Cobb; Lawrence M. Fodor, both of Bartlesville, Okla.

[73] Assignee: Phillips Petroleum Company, Bartlesville, Okla.

[21] Appl. No.: 969,599

[22] Filed: Dec. 14, 1978

[51] Int. Cl.$^2$ .............................................. C07C 3/52
[52] U.S. Cl. ................................... 585/452; 585/411
[58] Field of Search ............ 260/668 B, 671 R, 671 C

[56] References Cited

U.S. PATENT DOCUMENTS

| | | | |
|---|---|---|---|
| 2,688,044 | 8/1954 | Pines et al. | 260/668 B |
| 2,721,885 | 10/1955 | Pines et al. | 260/668 B |
| 2,721,886 | 10/1955 | Pines et al. | 260/668 B |
| 3,651,161 | 3/1972 | Waragai et al. | 260/671 C |
| 3,666,744 | 5/1972 | Black | 260/671 C |
| 3,691,242 | 9/1972 | Cheng | 260/668 B |
| 4,034,052 | 7/1977 | Puskas | 260/671 C |

*Primary Examiner*—Veronica O'Keefe

[57] ABSTRACT

A process whereby alkyl-substituted aromatics are alkylated with a monoolefin in the presence of an alkali metal catalyst and a promoter composition selected from the group consisting of (1) naphthalene, at least one tertiary amine, and at least one tertiary alcohol or alkali metal salt thereof, and (2) naphthalene and at least one tertiary alcohol or alkali metal salt thereof.

18 Claims, No Drawings

CATALYTIC ALKYLATION OF ALKYL-SUBSTITUTED AROMATICS WITH MONOOLEFINS

This invention relates to an improved process for the catalytic alkylation of alkyl-substituted aromatics with monoolefins. In another aspect this invention relates to an improved process for preparing tert-amyl benzene by the alkali metal catalyzed alkylation of cumene with ethylene.

The alkylation of alkyl-substituted aromatics with monoolefins has been the subject of a number of investigations and patents. Although different catalyst systems have been proposed for this process, an alkali metal catalyst system has been of particular interest since it permits alkyl aromatics with a benzylic carbon having a hydrogen substituent to be alkylated in the alkyl side chain. Much of the effort in this field has been directed toward discovering promoters that would increase the conversion and selectivity of the alkali metal catalyzed reaction.

An object of the present invention is to improve the conversion rate of the alkali metal catalyzed reaction.

Another object of the present invention is to improve the conversion rate of the alkali metal catalyzed reaction without adversely affecting the selectivity to desirable products.

Still another object of the present invention is to provide a process which enables the alkylation to proceed at a lower reaction temperature.

Other aspects, objects, and advantages of the present invention will become more apparent upon review of the following disclosure.

In accordance with the instant invention a process is provided comprising reacting a monoolefin hydrocarbon with an alkyl aromatic compound in the presence of an alkali metal catalyst and a promoter composition selected from the group consisting of (1) naphthalene, at least one tertiary amine, and at least one tertiary alcohol or alkali metal salt thereof, and (2) napthalene and at least one tertiary alcohol or alkali metal salt thereof.

Broadly, the type of alkyl aromatic compounds for which the present invention is applicable include any suitable alkyl aromatic compounds having a hydrogen atom bonded to at least one benzylic carbon of at least one alkyl group. Examples of suitable alkyl aromatic compounds include toluene, xylene, ethylbenzene, isopropylbenzene, n-propylbenzene, n-butylbenzene, isobutylbenzene, sec-butylbenzene, mesitylene, tetralin, and the like, and mixtures thereof. While the alkyl aromatic compounds can have other substituents which are unreactive under the alkylation conditions, it is preferred that the alkyl aromatic compounds be hydrocarbons. The especially preferred alkyl aromatic hydrocarbons are those having 1 to 4 alkyl substituents where each such alkyl substituent has 1 to 20 carbon atoms.

The monoolefin hydrocarbons include all those generally recognized as being suitable for alkali metal catalyzed alkylations of alkyl aromatics. Examples of typical such monoolefins include ethylene, propylene, 1-butene, isobutylene, 1-pentene, 1-hexene, 2-hexene, 3-hexene, 1-heptene, 2-heptene, 3-heptene, the four normal octenes, the four normal nonenes, 3-methyl-1-butene, 2-methyl-2-butene, tetramethylethylene, 1-methylcyclohexene, 1-ethylcyclohexene, 1-(1-propyl)-cyclohexene, 1,2-dimethylcyclohexene, 1,4-dimethylcyclohexene, 1,3,5-trimethylcyclohexene, and the like, and mixtures thereof. Generally for most syntheses ethylene and propylene are the preferred alkylating agents.

The alkali metals, viz. lithium, sodium, potassium, rubidium, and cesium are not equally active as catalysts. Generally, the activity of the alkali metals increases with their atomic weight. The more plentiful sodium and potassium, and mixtures thereof, such as sodium-potassium alloys, are currently preferred. Since sodium generally requires higher reaction temperatures the presently especially preferred alkali metal is potassium or a sodium-potassium alloy.

The alkali metal can be employed in any suitable form. Preferably in order to maximize surface area the alkali metal is employed in a particulate, powdered, or finely divided form. In an especially preferred embodiment the alkali metal is in a colloidal or near colloidal form, e.g. having average particle size in the range of about 0.5 to 1000 millimicrons. The preferred sodium-potassium alloys are those which are typically liquid at room temperature, i.e. those having 40 to 90 weight percent potassium. The alloy containing 78 weight percent potassium is especially preferred because it is an eutectic.

The term tertiary amine as used in this disclosure and in the appended claims denotes those amines having three hydrocarbyl radicals attached to each nitrogen. Generally it would be preferred to employ tertiary amines having no more than 60 carbon atoms per molecule. The presently preferred amines are those materials having the formula

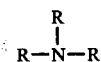

or the formula

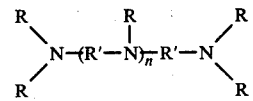

where R is a hydrocarbon radical of 1 to 6 carbon atoms, R' is a divalent hydrocarbyl radical of 1 to 6 carbon atoms, n is an integer in the range 0 to 6, and each R and R' can be the same or different. Typical tertiary amines corresponding to formula I are: trimethylamine, tri-ethylamine, tri-n-propylamine, tri-n-butylamine, tri-amylamine, dimethylbutylamine and trihexylamine. Typical polyalkylated polyamines corresponding to formula II are: N,N,N',N'tetramethylmethylenediamine, N,N,N',N'-tetraethylethylenediamine, N,N,N',N'-tetramethylethylenediamine, N,N,N',N'-tetrapropylpropylenediamine, N,N,N',N',N''pentamethyldimethylenetriamine, N,N,N',N',N''-pentamethyldiethylenetriamine, and the like and mixtures thereof. Other tertiary amines within the scope of this invention but not represented by the general formulas listed above are such tertiary amines as triethylenediamine.

The term tertiary alcohol as used in this disclosure and the following claims refers to those alcohols of the formula

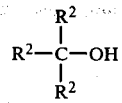

wherein each $R^2$ is a hydrocarbyl radical comprised of 1-4 carbon atoms and wherein each $R^2$ may be the same or different. Typical examples are tert-butyl alcohol, tert-amyl, alcohols, tert-hexyl, and so forth up to and including tert-dodecyl alcohols. Alkali metal salts of such tertiary alcohols can also be used as equivalents of the tertiary alcohols in the process.

The reaction conditions employed in the instant invention can vary widely depending upon the particular monoolefin and alkyl aromatics employed, the products desired, and the yields desired. Generally, the reaction temperature will be in the range of about 125° C. to about 225° C., preferably about 140° C. to about 175° C. Generally the pressure is maintained at a level sufficient to maintain the reactants in the liquid phase. Typically the reaction would thus be conducted with the pressure in the range of about 50 to about 1000 psig, preferably about 250 to about 600 psig, though higher pressures, e.g. as high as even 1200 psig, may be employed if desired, depending upon the reactants chosen, how the reactants are charged, and what reaction temperatures are chosen.

The reaction period can also vary widely depending upon the yield desired. Generally the reaction period will range from 1 hour to as much as 50 hours, or even longer. Because of the high production rates obtained with the use of novel catalyst system, the reaction period will be shorter than that found necessary heretofore to obtain equivalent yields and conversions.

The process can be carried out in any suitable equipment. The reaction can be carried out in either a batch or a continuous fashion, with the reactants brought into contact in any order of addition. In charging the reactants and in carrying out the reaction, care should be taken to exclude air or oxygencontaining gas and moisture which tends to adversely affect the reaction. This can be accomplished by purging the reactor with dry nitrogen or other dry, inert gas prior to charging it with the reactants and catalyst and by pressuring the reactants and catalyst into the reaction vessel with such gas.

The reactants can be dried and preheated if desired and introduced separately or as a mixture into the reaction zone. After the reaction is complete the reaction mixture can be cooled, gases and vapors vented therefrom, and the reaction mixture filtered to remove catalyst and support. The liquid reaction product can be fractionally distilled or otherwise separated to obtain the desired product. Unreacted reactants can be recovered and recycled to the reaction zone if desired. The catalyst and any metalated compounds present can be inactivated or decomposed, if desired, by adding to the reaction residue a polar (active hydrogen) compound, for example, water or an alcohol such as methanol or isopropanol.

The molar ratio of alkyl aromatic reactant to monoolefin reactant can vary widely. Generally, it is preferred to employ the monoolefin in an amount greater than the stoichiometric amount. Generally, therefore, the molar ratio of alkyl aromatic reactant to monoolefin is in the range of about 0.01 to about 20, more preferably about 0.3 to about 2.

The reaction can generally be carried out with or without a diluent. Generally the diluent can be any organic compound which does not have a detrimental effect upon the reaction. Examples include paraffins, cycloparaffins, and aromatics, the latter of which do not contain a hydrogen atom attached to a benzylic carbon atom. When employed the volume percent of diluent, based on the volume percent of the alkyl aromatic is in the range of about 10 to about 100. Also it is preferable if the diluent has a boiling point that is significantly different from that of the reactants and product so as to allow more easy separation of those materials, by means such as fractional distillation. Specific examples of suitable diluents include n-pentane, n-hexane, isooctane, cyclohexane, decahydronaphthalene, white oils, benzene, tertiary butylbenzene, tertiary amylbenzene, etc.

The amount of alkali metal catalyst used in the reaction will be any amount sufficient to catalyze the desired reaction. Generally the parts by weight of alkali metal employed for each 100 parts by weight of alkyl aromatic reactant will be in the range of about 0.01 to about 2, preferably about 1 to about 2.

The amount of the ingredients in the promoter composition can also vary widely. For every 100 parts by weight of alkyl aromatic reactant there is generally employed about 0.1 to about 5 parts by weight of naphthalene, about 0.1 to about 2 parts by weight of tertiary amine (when a tertiary amine is employed), and about 0.1 to about 2 parts by weight of tertiary alcohol, preferably about 0.2 to about 1 part by weight naphthalene, about 0.1 to about 1 part by weight tertiary amine (when employed), and about 0.1 to about 1 part by weight tertiary alcohol.

The instant invention and its advantages will now be further illustrated by the following examples:

EXAMPLE I

This example is a control wherein no initiator-promoter is used and is typical of the procedure used in this invention.

To a one-liter-stainless steel reactor (AE Magnestir Autoclave) equipped with a stirrer, thermocouple, and inlet tubes was charged 450 milliliters (388.8 grams) of cumene (isopropylbenzene), and about 4 to 7 grams of a 22 wt. % sodium-78 wt. % potassium catalyst. The closed reactor was then stirred while heated to 190° C. Ethylene (to about 500 psig) was pressured into the reactor. The temperature was controlled by adjusting heat controls, dropping the external heater or air cooling externally. After the ethylene pressure had dropped to about 200-250 psig, more ethylene was added (again to about 500 psig). After 2-3 hours, the pressure ceased to drop. During the run, a maximum temperature of 215° C. was reached. The reactor was quenched in icewater, the contents removed and the reactor washed with cyclohexane. The contents and washings were filtered under nitrogen and the filtrate distilled to recover the product tert-amylbenzene. A sample was obtained before filtering or washing and analyzed by GLC using a 304.8 centimeter (10 foot)×0.635 centimeter (0.25 inch) column packed with 5 wt. % SP1200 (silicone oil) and 1.75 wt. % Bentone 34 (treated clay) on a support of Supelcoport (Supelco, Inc.) which is an acid-washed silane treated diatomite support. The chromatograph was programmed from 150°-200° C. at 10°/min. using a 60 cubic centimeter per minute helium flow. Three such runs were made. Analyses averaged from the three runs indicated cumene was being coverted at a rate of 4.6 wt. %/hr. The product selectivity was 70.6 wt. % tert-amylbenzene, 28.4 wt. % 1,1-dimethylindane, and 1.5 wt. % 1,1-dimethyl-3-ethylindane.

EXAMPLE II

This example is another control illustrating the effects of adding a polynuclear hydrocarbon initiator-promoter.

The reaction described in Example I was repeated except 1 gram of naphthalene was added to the reactor. The reaction was initiated at a much lower temperature than in Example I, 157° C., and cumene was consumed at a faster rate than in Example I, 24.2 wt. %/hr. The selectivity of tert-amylbenzene (TAB) was increased to 88.5 wt. % with only 5.5 wt. % 1,1-dimethylindane (DMI). The reaction was repeated but 4 grams of naphthalene was used. The cumene conversion was 48.2 wt. % with a selectivity of 79.1 wt. % TAB, 5.1 wt. % 1,1-dimethyl-3-ethylindane (EDMI) and 13.2 wt. % 1,1-diethyl-3,3-dimethylindane (DEDMI).

EXAMPLE III

This example illustrates the invention and shows the effect tertiary amines and tertiary alcohols have on the rate of cumene conversion and selectivity to TAB when used separately with naphthalene and both in combination with naphthalene.

In this example the reaction as described in Example II was repeated except with the addition of amine and/or alcohol as indicated in Table I below. The results of Examples I and II are included in Table I for comparative purposes.

Table I

| | Conversion of Cumene and Ethylene to Tert-Amylbenzene | | | | | | | | |
|---|---|---|---|---|---|---|---|---|---|
| | Promoter, grams | | | Reaction | Cumene | % Selectivity by GLC | | | |
| Example | Naph[a] | TEA[b] | t-BuOH[c] | Temp., °C. | Conv., %/hr. | TAB[d] | DMI[e] | EDMI[f] | DEDMI[g] |
| I | — | — | — | 190–215 | 4.6[h] | 70.6[h] | 28.4[h] | 1.5[h] | — |
| II-A | 1.0 | — | — | 157–163 | 24.2 | 88.5 | 5.5 | 4.9 | 1.0 |
| II-B | 4.0 | — | — | 161–178 | 48.2 | 79.1 | — | 5.1 | 13.2 |
| III-A | 2.0 | 0.7 | — | 155–166 | 35.5 | 90.1 | — | 6.2 | 3.4 |
| III-B | 2.0 | 2.2 | — | 155–167 | 37.3 | 90.1 | — | 5.8 | 3.8 |
| Inventive Runs: | | | | | | | | | |
| III-C | 2.0 | — | 1.6 | 155–172 | 60.7 | 91.2 | — | 2.7 | 4.7 |
| III-D | 2.0 | 1.5 | 1.6 | 156–173 | 48.8 | 94.5 | — | 0.7 | 3.2 |
| III-E | 2.0 | 2.2 | 1.6 | 157–175 | 65.7 | 93.1 | — | — | 4.5 |
| III-F | 2.0 | 2.2 | 2.3 | 157–165 | 48.0 | 95.2 | — | 0.7 | 2.6 |
| III-G | 2.0 | 3.6 | 2.3 | 155–178 | 49.3 | 97.4 | — | — | 1.1 |

[a] Naphthalene
[b] Triethylamine
[c] Tertiary butyl alcohol
[d] Tertiary amylbenzene
[e] 1,1-Dimethylindane
[f] 1,1-Dimethyl-3-ethylindane
[g] 1,1-Diethyl-3,3-dimethylindane
[h] Average of 3 values.

The above data shows that triethylamine alone increases the selectivity to TAB while slightly decreasing the conversion rate of cumene. The tertiary butyl alcohol increases both the conversion rate and the selectivity to TAB. The combination of triethylamine and tertiary butyl alcohol yields better selectivity than provided by either used alone.

From the foregoing description and illustrative examples, one skilled in the art can easily ascertain the essential characteristics of this invention and without departing from the spirit and scope thereof, can make various changes and modifications of the invention to adapt it to various usages and conditions. Consequently, such changes and modifications should be viewed as being within the range of equivalents of the following claims.

What is claimed is:

1. A process comprising reacting a monoolefin hydrocarbon with an alkyl aromatic compound having a hydrogen bonded to at least one benzylic carbon of at least one alkyl group in the presence of a catalytic amount of alkali metal and a conversion promoting amount of a promoter composition comprising naphthalene, and at least one tertiary alcohol of the formula

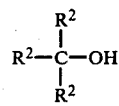

wherein each $R^2$ is a hydrocarbyl radical having 1 to 4 carbon atoms and wherein each $R^2$ may be the same of different, or alkali metal salt of said tertiary alcohol, under such reaction conditions that at least one benzylic carbon of said alkyl aromatic compound is alkylated.

2. A process according to claim 1 wherein said promoter composition includes at least one tertiary amine.

3. A process according to claim 2 wherein said tertiary amine is selected from those having the formula

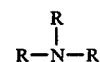

or the formula

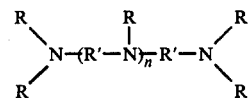

wherein R is a hydrocarbyl radical of 1 to 6 carbon atoms, R' is a divalent hydrocarbyl radical of 1 to 6 carbon atoms, n is an integer in the range of 0 to 6, and each R and R' can be the same or different.

4. A process according to claim 3 wherein for each 100 parts by weight of alkyl aromatic compound there is employed about 0.1 to about 5 parts by weight of naphthalene, about 0.1 to about 2 parts by weight of said tertiary amine, about 0.1 to about 2 parts by weight of said tertiary alcohol or alkali metal salt of said tertiary alcohol, and about 1 to about 2 parts by weight of alkali metal.

5. A process according to claim 4 wherein said reaction is carried out at a temperature in the range of about 125° C. to about 225° C. and a pressure of about 50 to about 1000 psig.

6. A process according to claim 5 wherein said alkyl aromatic compound is an alkyl aromatic hydrocarbon having 1 to 4 alkyl substituents each having 1 to 20 carbon atoms.

7. A process according to claim 6 wherein said monoolefin hydrocarbon is selected from propylene and ethylene.

8. A process according to claim 7 wherein said alkyl aromatic hydrocarbon is cumene and said monoolefin hydrocarbon is ethylene.

9. A process according to claim 8 wherein said reaction is carried out a temperature in the range of about 140° C. to about 175° C. and a pressure of about 250 to about 6000 psig.

10. A process according to claim 9 wherein said tertiary amine is triethylamine.

11. A process according to claim 10 wherein said tertiary alcohol is tert-butyl alcohol.

12. A process according to claim 11 wherein for each 390 parts by weight of cumene there is employed about 2 parts by weight of naphthalene, about 1.5 to about 3.6 parts by weight of triethylamine, and about 1.6 to about 2.3 parts by weight of tert-butyl alcohol.

13. A process according to claim 12 wherein about 22 weight percent of the alkali metal is sodium and about 78 weight percent of the alkali metal is potassium.

14. A process according to claim 7 wherein said tertiary amine is triethylamine.

15. A process according to claim 14 wherein said tertiary alcohol is tert-butyl alcohol.

16. A process according to claim 14 wherein said tertiary alcohol is tert-amyl alcohol.

17. A process according to claim 1 wherein said promoter composition consists essentially of naphthalene and said at least one tertiary alcohol or alkali metal salt of said alcohol.

18. A process according to claim 17 wherein said promoter composition consists essentially on naphthalene and tertiary butyl alcohol.

* * * * *